(12) United States Patent
Farris et al.

(10) Patent No.: US 10,376,647 B2
(45) Date of Patent: Aug. 13, 2019

(54) ANTI-ROTATION MECHANISM FOR TELESCOPIC SCREW ASSEMBLY

(71) Applicant: MEDIMOP Medical Projects Ltd., Ra'anana (IL)

(72) Inventors: Jason W. Farris, Gilbert, AZ (US); Jorge Santos, Scottsdale, AZ (US); Tommy Gene Davis, Athens, TX (US)

(73) Assignee: West Pharma. Services IL, Ltd., Ra'anana (IL)

( * ) Notice: Subject to any disclaimer, the term of this patent is extended or adjusted under 35 U.S.C. 154(b) by 627 days.

(21) Appl. No.: 15/074,412

(22) Filed: Mar. 18, 2016

(65) Prior Publication Data
US 2017/0266385 A1    Sep. 21, 2017

(51) Int. Cl.
*A61M 5/315*    (2006.01)
*F16H 25/20*    (2006.01)

(52) U.S. Cl.
CPC .... *A61M 5/31505* (2013.01); *A61M 5/31511* (2013.01); *A61M 5/31528* (2013.01);
(Continued)

(58) Field of Classification Search
CPC .......... A61M 5/31511; A61M 5/31505; A61M 5/31528; A61M 5/31581; A61M 5/31586;
(Continued)

(56) References Cited

U.S. PATENT DOCUMENTS

| | | |
|---|---|---|
| 232,432 A | 9/1880 | Allison |
| 1,795,630 A | 3/1931 | Wilson |

(Continued)

FOREIGN PATENT DOCUMENTS

| | | |
|---|---|---|
| CN | 1505535 A | 6/2004 |
| CN | 101227943 A | 7/2008 |

(Continued)

OTHER PUBLICATIONS

West Introduces The Daikyo Crystal Zenith RU Prefillable Syringe, Pharmaceutical Online, Jun. 2008, downloaded from webpage: http://www.pharmaceuticalonline.com/article.mvc/west-introduces-prefillable-syringe-system, Download date: Jan. 2009, original posting date: Jun. 2008, 2 pages.

(Continued)

*Primary Examiner* — Imani N Hayman
*Assistant Examiner* — Tiffany Legette
(74) *Attorney, Agent, or Firm* — Panitch Schwarze Belisario & Nadel LLP

(57) ABSTRACT

An injection assembly includes a housing with a barrel positioned within the housing. The barrel includes an axis extending from a proximal end to a distal end thereof and a chamber for storing medicine. An elongate anti-rotation shaft is rotationally fixed to the housing and has a non-circular cross-section. The injection assembly includes an inner screw having an inner screw opening to complementarily receive the anti-rotation shaft to prevent rotation of the inner screw with respect to the anti-rotation shaft but allow respective linear translation along the axis. An outer screw is positioned within, and rotatable with respect to, the housing and has an outer screw opening to threadably receive the inner screw, wherein rotation of the outer screw translates the inner screw along the axis and along the anti-rotation shaft. A plunger is coupled to the distal end of the inner screw and is moveable with respect to the chamber to push the medicine out of the chamber when the outer screw is rotated.

17 Claims, 4 Drawing Sheets

(52) U.S. Cl.
CPC .... *A61M 5/31581* (2013.01); *A61M 5/31586* (2013.01); *A61M 5/31591* (2013.01); *F16H 25/2056* (2013.01); *A61M 2005/3152* (2013.01); *A61M 2005/31508* (2013.01); *A61M 2005/31518* (2013.01); *A61M 2005/31598* (2013.01)

(58) Field of Classification Search
CPC . A61M 2005/31518; A61M 2005/3152; F16H 25/2056
See application file for complete search history.

(56) References Cited

U.S. PATENT DOCUMENTS

| | | | |
|---|---|---|---|
| 2,677,373 A | 5/1954 | Barradas |
| 2,702,547 A | 2/1955 | Glass |
| 2,860,635 A | 11/1958 | Wilburn |
| 3,203,269 A | 8/1965 | Perrine |
| 3,212,685 A | 10/1965 | Swan et al. |
| 3,623,474 A | 11/1971 | Heilman et al. |
| 4,195,636 A | 4/1980 | Behnke |
| 4,254,768 A | 3/1981 | Ty |
| 4,273,122 A | 6/1981 | Whitney et al. |
| 4,300,554 A | 11/1981 | Hessberg et al. |
| 4,403,987 A | 9/1983 | Gottinger |
| 4,435,173 A | 3/1984 | Siposs et al. |
| 4,465,478 A | 8/1984 | Sabelman et al. |
| 4,502,488 A | 3/1985 | Degironimo et al. |
| 4,504,263 A | 3/1985 | Steuer et al. |
| 4,564,054 A | 1/1986 | Gustavsson |
| 4,585,439 A | 4/1986 | Michel |
| 4,599,082 A | 7/1986 | Grimard |
| 4,664,654 A | 5/1987 | Strauss |
| 4,685,903 A | 8/1987 | Cable et al. |
| 4,698,055 A | 10/1987 | Sealfon |
| 4,735,311 A | 4/1988 | Lowe et al. |
| 4,810,215 A | 3/1989 | Kaneko |
| 4,867,743 A | 9/1989 | Vaillancourt |
| 4,882,575 A | 11/1989 | Kawahara |
| 4,892,521 A | 1/1990 | Laico et al. |
| 4,919,596 A | 4/1990 | Slate et al. |
| 4,964,866 A | 10/1990 | Szwarc |
| 5,051,109 A | 9/1991 | Simon |
| 5,112,317 A | 5/1992 | Michel |
| 5,190,521 A | 3/1993 | Hubbard et al. |
| 5,300,045 A | 4/1994 | Plassche, Jr. |
| 5,318,522 A | 6/1994 | D'Antonio |
| 5,478,315 A | 12/1995 | Brothers et al. |
| 5,501,665 A | 3/1996 | Jhuboo et al. |
| 5,562,624 A | 10/1996 | Righi et al. |
| 5,624,400 A | 4/1997 | Firth et al. |
| 5,637,095 A | 6/1997 | Nason et al. |
| 5,643,218 A | 7/1997 | Lynn et al. |
| 5,645,530 A | 7/1997 | Boukhny et al. |
| 5,647,853 A | 7/1997 | Feldmann et al. |
| 5,658,256 A | 8/1997 | Shields |
| 5,662,678 A | 9/1997 | Macklin |
| 5,728,075 A | 3/1998 | Levander |
| 5,766,186 A | 6/1998 | Faraz et al. |
| 5,810,784 A | 9/1998 | Tamaro |
| 5,830,187 A | 11/1998 | Kriesel et al. |
| 5,851,197 A | 12/1998 | Marano et al. |
| 5,858,001 A | 1/1999 | Tsals et al. |
| 5,893,842 A | 4/1999 | Imbert |
| 5,894,015 A | 4/1999 | Rechtin |
| 5,919,167 A | 7/1999 | Mulhauser et al. |
| 5,926,596 A | 7/1999 | Edwards et al. |
| 5,944,699 A | 8/1999 | Barrelle et al. |
| 5,968,011 A | 10/1999 | Larsen et al. |
| 5,989,221 A | 11/1999 | Hjertman |
| 5,993,423 A | 11/1999 | Choi |
| 6,033,245 A | 3/2000 | Yamkovoy |
| 6,045,533 A | 4/2000 | Kriesel et al. |
| 6,186,982 B1 | 2/2001 | Gross et al. |
| 6,200,296 B1 | 3/2001 | Dibiasi et al. |
| 6,248,093 B1 | 6/2001 | Moberg |
| 6,270,481 B1 | 8/2001 | Mason et al. |
| 6,287,283 B1 | 9/2001 | Ljunggreen et al. |
| 6,302,633 B1 | 10/2001 | Poe |
| 6,485,461 B1 | 11/2002 | Mason et al. |
| 6,485,465 B2 | 11/2002 | Moberg et al. |
| 6,511,336 B1 | 1/2003 | Turek et al. |
| 6,554,800 B1 | 4/2003 | Nezhadian et al. |
| 6,565,541 B2 | 5/2003 | Sharp |
| 6,595,956 B1 | 7/2003 | Gross et al. |
| 6,656,159 B2 | 12/2003 | Flaherty |
| 6,659,980 B2 | 12/2003 | Moberg et al. |
| 6,699,218 B2 | 3/2004 | Flaherty et al. |
| 6,722,916 B2 | 4/2004 | Buccinna et al. |
| 6,743,211 B1 | 6/2004 | Prausnitz et al. |
| 6,749,587 B2 | 6/2004 | Flaherty |
| 6,800,071 B1 | 10/2004 | McConnell et al. |
| 6,905,298 B1 | 6/2005 | Haring |
| 6,960,192 B1 | 11/2005 | Flaherty et al. |
| 6,997,727 B1 | 2/2006 | Legrady et al. |
| 7,033,338 B2 | 4/2006 | Vilks et al. |
| 7,034,223 B2 | 4/2006 | Fan et al. |
| 7,060,054 B2 | 6/2006 | Nissels |
| 7,225,694 B2 | 6/2007 | Said |
| 7,250,037 B2 | 7/2007 | Shermer et al. |
| 7,291,132 B2 | 11/2007 | DeRuntz et al. |
| 7,291,159 B2 | 11/2007 | Schmelzeisen-Redeker et al. |
| 7,407,493 B2 | 8/2008 | Cane' |
| 7,442,186 B2 | 10/2008 | Blomquist |
| 7,488,181 B2 | 2/2009 | van Haaster |
| 7,501,587 B2 | 3/2009 | English |
| 7,503,786 B2 | 3/2009 | Kato et al. |
| 7,540,858 B2 | 6/2009 | DiBiasi |
| 7,704,088 B2 | 4/2010 | Sakamoto |
| 7,717,903 B2 | 5/2010 | Estes et al. |
| 7,736,344 B2 | 6/2010 | Moberg et al. |
| 7,766,867 B2 | 8/2010 | Lynch et al. |
| 7,794,426 B2 | 9/2010 | Briones et al. |
| 7,938,803 B2 | 5/2011 | Mernoe et al. |
| 7,967,795 B1 | 6/2011 | Cabiri |
| 8,057,436 B2 | 11/2011 | Causey et al. |
| 8,062,253 B2 | 11/2011 | Nielsen et al. |
| 8,105,293 B2 | 1/2012 | Pickhard |
| 8,152,779 B2 | 4/2012 | Cabiri |
| 8,157,769 B2 | 4/2012 | Cabiri |
| 8,172,591 B2 | 5/2012 | Wertz |
| 8,177,749 B2 | 5/2012 | Slate et al. |
| 8,221,356 B2 | 7/2012 | Enggaard et al. |
| 8,348,898 B2 | 1/2013 | Cabiri |
| 8,425,468 B2 | 4/2013 | Weston |
| 8,512,295 B2 | 8/2013 | Evans et al. |
| 8,523,803 B1 | 9/2013 | Favreau |
| 8,551,046 B2 | 10/2013 | Causey et al. |
| 8,562,364 B2 | 10/2013 | Lin et al. |
| 8,603,026 B2 | 12/2013 | Favreau |
| 8,603,027 B2 | 12/2013 | Favreau |
| 8,622,966 B2 | 1/2014 | Causey et al. |
| 8,915,882 B2 | 12/2014 | Cabiri |
| 8,979,802 B2 | 3/2015 | Woehr |
| 9,011,164 B2 | 4/2015 | Filman et al. |
| 9,072,827 B2 | 7/2015 | Cabiri |
| 9,149,575 B2 | 10/2015 | Cabiri |
| 9,173,997 B2 | 11/2015 | Gross et al. |
| D747,799 S | 1/2016 | Norton et al. |
| 9,259,532 B2 | 2/2016 | Cabiri |
| 9,314,569 B2 | 4/2016 | Causey et al. |
| 9,345,836 B2 | 5/2016 | Cabiri et al. |
| 9,350,634 B2 | 5/2016 | Fadell |
| 9,393,365 B2 | 7/2016 | Cabiri |
| 9,421,323 B2 | 8/2016 | Cabiri et al. |
| 9,452,261 B2 | 9/2016 | Alon |
| 9,522,234 B2 | 12/2016 | Cabiri |
| 9,539,388 B2 | 1/2017 | Causey et al. |
| 9,572,926 B2 | 2/2017 | Cabiri |
| 9,656,019 B2 | 5/2017 | Cabiri et al. |
| 9,782,545 B2 | 10/2017 | Gross et al. |
| 2001/0018937 A1 | 9/2001 | Nemoto |
| 2001/0025168 A1 | 9/2001 | Gross et al. |

(56) References Cited

U.S. PATENT DOCUMENTS

| | | |
|---|---|---|
| 2001/0034502 A1 | 10/2001 | Moberg et al. |
| 2001/0041869 A1 | 11/2001 | Causey et al. |
| 2002/0016569 A1 | 2/2002 | Critchlow et al. |
| 2002/0029018 A1 | 3/2002 | Jeffrey |
| 2002/0151855 A1 | 10/2002 | Douglas et al. |
| 2002/0169215 A1 | 11/2002 | Meng |
| 2003/0009133 A1 | 1/2003 | Ramey |
| 2003/0014018 A1 | 1/2003 | Giambattista et al. |
| 2003/0216683 A1 | 11/2003 | Shekalim |
| 2004/0000818 A1 | 1/2004 | Preuthun et al. |
| 2004/0049160 A1 | 3/2004 | Hsieh et al. |
| 2004/0082911 A1 | 4/2004 | Tiu et al. |
| 2004/0092873 A1 | 5/2004 | Moberg |
| 2004/0127857 A1 | 7/2004 | Shemesh et al. |
| 2004/0210196 A1 | 10/2004 | Bush, Jr. et al. |
| 2005/0033234 A1 | 2/2005 | Sadowski et al. |
| 2005/0038391 A1 | 2/2005 | Wittland et al. |
| 2005/0171512 A1 | 8/2005 | Flaherty |
| 2005/0203461 A1 | 9/2005 | Flaherty et al. |
| 2005/0283114 A1 | 12/2005 | Bresina et al. |
| 2006/0124269 A1 | 6/2006 | Miyazaki et al. |
| 2006/0206054 A1 | 9/2006 | Shekalim |
| 2006/0206057 A1* | 9/2006 | DeRuntz ........... A61M 5/31551 604/224 |
| 2006/0264888 A1 | 11/2006 | Moberg et al. |
| 2006/0264890 A1 | 11/2006 | Moberg et al. |
| 2006/0293722 A1 | 12/2006 | Slatkine et al. |
| 2007/0025879 A1 | 2/2007 | Vandergaw |
| 2007/0073228 A1 | 3/2007 | Mernoe et al. |
| 2007/0118405 A1 | 5/2007 | Campbell et al. |
| 2007/0167912 A1 | 7/2007 | Causey et al. |
| 2007/0179444 A1 | 8/2007 | Causey et al. |
| 2007/0185449 A1 | 8/2007 | Mernoe |
| 2007/0197954 A1 | 8/2007 | Keenan |
| 2007/0203454 A1 | 8/2007 | Shermer et al. |
| 2008/0033367 A1 | 2/2008 | Haury et al. |
| 2008/0033393 A1 | 2/2008 | Edwards et al. |
| 2008/0097381 A1 | 4/2008 | Moberg et al. |
| 2008/0215013 A1 | 9/2008 | Felix-Faure |
| 2008/0319383 A1 | 12/2008 | Byland et al. |
| 2009/0012478 A1 | 1/2009 | Weston |
| 2009/0076383 A1 | 3/2009 | Toews et al. |
| 2009/0088694 A1 | 4/2009 | Carter et al. |
| 2009/0093763 A1 | 4/2009 | Gonnelli et al. |
| 2009/0093792 A1 | 4/2009 | Gross et al. |
| 2009/0093793 A1 | 4/2009 | Gross et al. |
| 2009/0143730 A1 | 6/2009 | De Polo et al. |
| 2009/0204076 A1 | 8/2009 | Liversidge |
| 2009/0299288 A1 | 12/2009 | Sie et al. |
| 2009/0299290 A1 | 12/2009 | Moberg |
| 2009/0326459 A1 | 12/2009 | Shipway et al. |
| 2010/0076382 A1 | 3/2010 | Weston |
| 2010/0168683 A1 | 7/2010 | Cabiri |
| 2011/0066131 A1 | 3/2011 | Cabiri |
| 2011/0092915 A1 | 4/2011 | Olson et al. |
| 2011/0112504 A1 | 5/2011 | Causey et al. |
| 2011/0224616 A1 | 9/2011 | Slate et al. |
| 2012/0022496 A1 | 1/2012 | Causey et al. |
| 2012/0041387 A1 | 2/2012 | Bruggemann et al. |
| 2012/0172817 A1 | 7/2012 | Bruggemann et al. |
| 2013/0085457 A1 | 4/2013 | Schiff et al. |
| 2013/0110049 A1 | 5/2013 | Cronenberg et al. |
| 2013/0190693 A1 | 7/2013 | Ekman et al. |
| 2013/0245596 A1 | 9/2013 | Cabiri et al. |
| 2013/0267895 A1 | 10/2013 | Hemmingsen |
| 2013/0296799 A1 | 11/2013 | Degtiar et al. |
| 2013/0304021 A1* | 11/2013 | Cabiri ................ A61M 5/31511 604/506 |
| 2013/0310753 A1 | 11/2013 | Cabiri |
| 2013/0331791 A1 | 12/2013 | Gross et al. |
| 2014/0018735 A1 | 1/2014 | Causey et al. |
| 2014/0121633 A1 | 5/2014 | Causey et al. |
| 2014/0148784 A1 | 5/2014 | Anderson et al. |
| 2014/0174223 A1 | 6/2014 | Gross et al. |
| 2014/0194854 A1 | 7/2014 | Tsals |
| 2014/0236087 A1 | 8/2014 | Alderete, Jr. et al. |
| 2015/0119798 A1 | 4/2015 | Gross et al. |
| 2015/0374926 A1 | 12/2015 | Gross et al. |
| 2016/0030665 A1 | 2/2016 | Cabiri |
| 2016/0296716 A1 | 10/2016 | Cabiri et al. |
| 2016/0346478 A1 | 12/2016 | Bar-El et al. |

FOREIGN PATENT DOCUMENTS

| | | |
|---|---|---|
| CN | 101448536 A | 6/2009 |
| CN | 101522235 A | 9/2009 |
| CN | 101541362 A | 9/2009 |
| CN | 201692438 U | 1/2011 |
| CN | 102378638 A | 3/2012 |
| DE | 1064693 B | 9/1959 |
| DE | 19717107 A1 | 11/1998 |
| EP | 1003581 B1 | 11/2000 |
| EP | 1219312 A2 | 7/2002 |
| EP | 1530979 A1 | 5/2005 |
| FR | 2770136 A1 | 4/1999 |
| JP | H09-505758 A | 6/1997 |
| JP | 2002528676 A | 9/2002 |
| JP | 2009502273 A | 1/2009 |
| WO | 9307922 A1 | 4/1993 |
| WO | 9407553 A1 | 4/1994 |
| WO | 9700091 A1 | 1/1997 |
| WO | 200130421 A2 | 5/2001 |
| WO | 200172357 A2 | 10/2001 |
| WO | 0187384 A1 | 11/2001 |
| WO | 200238204 A2 | 5/2002 |
| WO | 02070182 A1 | 9/2002 |
| WO | 04000397 A1 | 12/2003 |
| WO | 2004105841 A1 | 12/2004 |
| WO | 2005072795 A2 | 8/2005 |
| WO | 2006037434 A1 | 4/2006 |
| WO | 06069380 A1 | 6/2006 |
| WO | 2006121921 A2 | 11/2006 |
| WO | 2007017052 A1 | 2/2007 |
| WO | 2007051563 A1 | 5/2007 |
| WO | 20070073228 A1 | 6/2007 |
| WO | 2009044401 | 4/2009 |
| WO | 2009144085 A2 | 12/2009 |
| WO | 2010089313 A1 | 8/2010 |
| WO | 2011090956 A2 | 7/2011 |
| WO | 2015114158 A1 | 8/2015 |

OTHER PUBLICATIONS

Copaxone®, Innovative Drugs, Teva Pharmaceuticals, downloaded from webpage: http://tevapharm.com/copaxone/, Download date: Jan. 2009, original posting date: unknown, 3 pages.

Office Action dated Apr. 5, 2010 in U.S. Appl. No. 12/244,666 by Gross.

Office Action dated Sep. 21, 2010 in U.S. Appl. No. 12/244,666 by Gross.

Office Action dated Jul. 7, 2014 in U.S. Appl. No. 12/244,666 by Gross.

Office Action dated Mar. 10, 2015 in U.S. Appl. No. 12/244,666 by Gross.

Office Action dated Sep. 18, 2015 in U.S. Appl. No. 13/874,085 by Cabiri.

Office Action dated May 25, 2016 in U.S. Appl. No. 14/874,017 by Cabiri.

Office Action dated Jun. 10, 2016 in U.S. Appl. No. 13/964,651 by Gross.

Office Action dated May 31, 2016 in U.S. Appl. No. 14/593,051 by Gross.

Int'l Search Report and Written Opinion dated May 13, 2009 in Int'l Application No. PCT/IL2008/001312.

Int'l Preliminary Report on Patentability dated Apr. 7, 2010 in Int'l Application No. PCT/IL2008/001312.

Office Action dated Sep. 30, 2010 in U.S. Appl. No. 12/689,250, by Cabiri.

Office Action dated May 3, 2012 in CN Application No. 200880117084. X.

(56) References Cited

OTHER PUBLICATIONS

Office Action dated Jan. 30, 2013 in CN Application No. 200880117084.X.
Office Action dated Aug. 15, 2013 in CN Application No. 200880117084.X.
Office Action dated Mar. 5, 2014 in CN Application No. 200880117084.X.
Office Action dated Feb. 20, 2015 in U.S. Appl. No. 13/521,181, by Cabiri.
Office Action dated Jul. 31, 2015 in U.S. Appl. No. 13/521,181, by Cabiri.
Extended Search Report dated Feb. 23, 2015 in EP Application No. 14166596.8.
Search Report dated Nov. 24, 2015 in EP Application No. 14166592.7.
Extended Search Report dated Mar. 8, 2016 in EP Application No. 14166592.7.
Extended Search Report dated Feb. 23, 2015 in EP Application No. 14166591.9.
Office Action dated Jan. 8, 2013 in JP Application No. 2010-527595.
Int'l Search Report dated Oct. 12, 2011 in Int'l Application No. PCT/US11/21605.
Int'l Written Opinion dated Jul. 19, 2012 in Int'l Application No. PCT/US11/21605.
Int'l Preliminary Report on Patentability dated Feb. 7, 2013 in Int'l Application No. PCT/US11/21605.
Office Action dated Sep. 2, 2014 in JP Application No. 2012-550069.
Office Action dated Nov. 5, 2013 in JP Application No. 2010-527595.
Office Action dated Jun. 3, 2014 in JP Application No. 2010-527595.
Office Action dated May 7, 2015 in JP Application No. 2012-550069.
Office Action dated Apr. 5, 2010 in U.S. Appl. No. 12/244,688 by Gross.
Office Action dated Sep. 2, 2010 in U.S. Appl. No. 12/244,688 by Gross.
Extended Search Report dated Aug. 7, 2014 in EP Application No. 14171477.4.
Office Action dated Aug. 6, 2014 in EP Application No. 11707942.
Office Action dated Feb. 4, 2014 in EP Application No. 11707942.
Office Action dated Dec. 1, 2015 in CN Application No. 2014102892041.
Office Action dated Apr. 22, 2016 in CN Application No. 2014102892041.
Office Action dated May 5, 2015 in CN Application No. 201180006571.0.
Office Action dated Nov. 2, 2014 in CN Application No. 201180006571.0.
Office Action dated Feb. 28, 2014 in CN Application No. 201180006571.0.
Int'l Search Report and Written Opinion dated Jul. 6, 2017 in Int'l Application No. PCT/US2017/022966.
Extended European Search Report dated Jul. 3, 2017 in EP Application No. 16190054.3.

* cited by examiner

ANTI-ROTATION MECHANISM FOR TELESCOPIC SCREW ASSEMBLY

BACKGROUND OF THE INVENTION

The present invention relates generally to a telescopic screw assembly and more particularly to a telescopic screw assembly with an anti-rotation mechanism.

Injectors deliver specified quantities of drugs or medicine to a patient and typically include a chamber for storing the drug, a needle connected to the chamber through which the drug is delivered, and a plunger which pushes the medicine from the chamber through the needle. One device for pushing the drug through the chamber is a manually activated plunger. The user typically holds the syringe between two fingers and activates or pushes the plunger with a thumb. One drawback of a manually activated plunger is that patients must be relatively dexterous and have the required hand strength to push the plunger themselves. Another apparatus for pushing the plunger through the chamber is a telescopic assembly. A telescopic assembly is generally contained within the syringe or injector and contains a plurality of nested, threaded members which expand via rotation to push the plunger through the chamber. One drawback of a telescopic assembly is that the rotation of the telescopic assembly must be counteracted to ensure that the assembly achieves full extension. Typical approaches to counteract the rotation include a stopper connected to the outer surface of the telescopic screw assembly. However, such features are susceptible to failure and may prevent the injector from delivering a full dose.

The present invention addresses the challenges associated with effectively preventing rotation of at least the center portion of a telescopic screw assembly.

BRIEF SUMMARY OF THE INVENTION

Briefly stated, one aspect of the present invention is directed to an injection assembly including a housing with a barrel positioned in the housing. The barrel includes an axis extending between a proximal end and a distal end of the barrel. The barrel also includes a chamber for storing medicine. An elongate anti-rotation shaft is rotationally fixed to the housing and has a non-circular cross section. The injection assembly includes an inner screw having an inner screw opening to complementarily receive the anti-rotation shaft to prevent rotation of the inner screw with respect to the anti-rotation shaft but allow respective linear translation along the axis. A rotatable outer screw is within the housing and includes an outer screw opening to threadably receive the inner screw. Rotation of the outer screw translates the inner screw along the axis and along the anti-rotation shaft. A plunger is coupled to a distal end of the inner screw and moveable with respect to the chamber to push the medicine out of the chamber when the outer screw is rotated.

Another aspect of the present invention is directed to an injection assembly comprising a housing with a barrel, an elongate anti-rotation shaft, an inner screw, an intermediary screw, and an outer screw positioned in the housing. The barrel includes an axis extending between a proximal end and a distal end of the barrel. The barrel also includes a chamber for storing medicine. The elongate anti-rotation shaft is rotationally fixed to the housing and has a non-circular cross section. The inner screw has an inner screw opening to complementarily receive the anti-rotation shaft to prevent rotation of the inner screw with respect to the anti-rotation shaft but allow respective linear translation along the axis. The intermediary screw includes an intermediary screw opening with an intermediary screw internal thread threadably engageable with the inner screw external thread such that rotation of the intermediary screw moves the inner screw along the axis and along the anti-rotation shaft. The intermediary screw also includes an intermediary screw external thread. The outer screw is rotatable with respect to the housing and has an outer screw opening to receive the intermediary screw. The outer screw opening includes an outer screw internal thread engageable with the intermediary screw external thread such that rotation of the outer screw moves the intermediary screw along the axis and rotates the intermediary screw. A plunger is coupled to a distal end of the inner screw and is moveable with respect to the chamber to push the medicine out of the chamber when the outer screw is rotated.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there shown in the drawings embodiments of the injection assembly which are presently preferred. It should be understood, however, that the invention is not limited to the precise arrangements and instrumentalities shown. In the drawings.

DETAILED DESCRIPTION OF THE INVENTION

Figure 1:
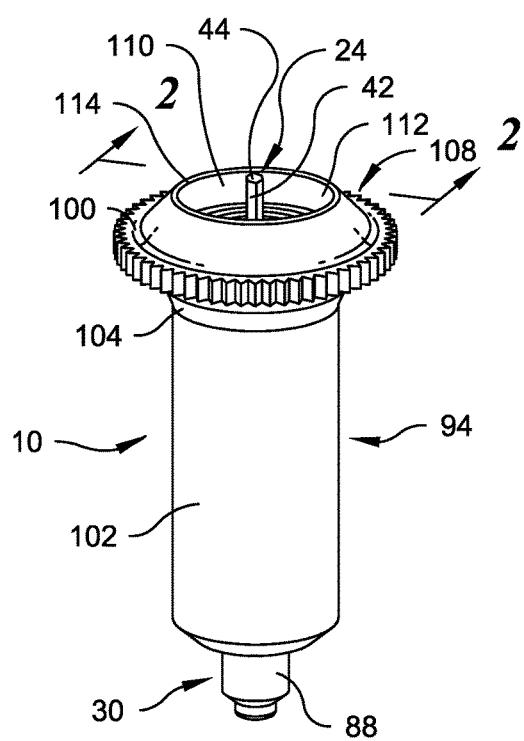
FIG. 1 is a front perspective view of a telescopic screw assembly in a contracted configuration in accordance with one embodiment of the present invention.
Figure 2:
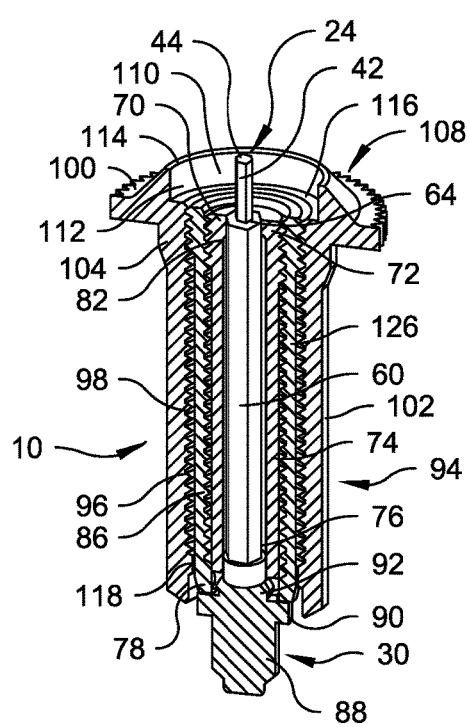
FIG. 2 is a perspective sectional view taken along line 2-2 of the telescopic screw assembly of FIG. 1 in a contracted state.
Figure 3:
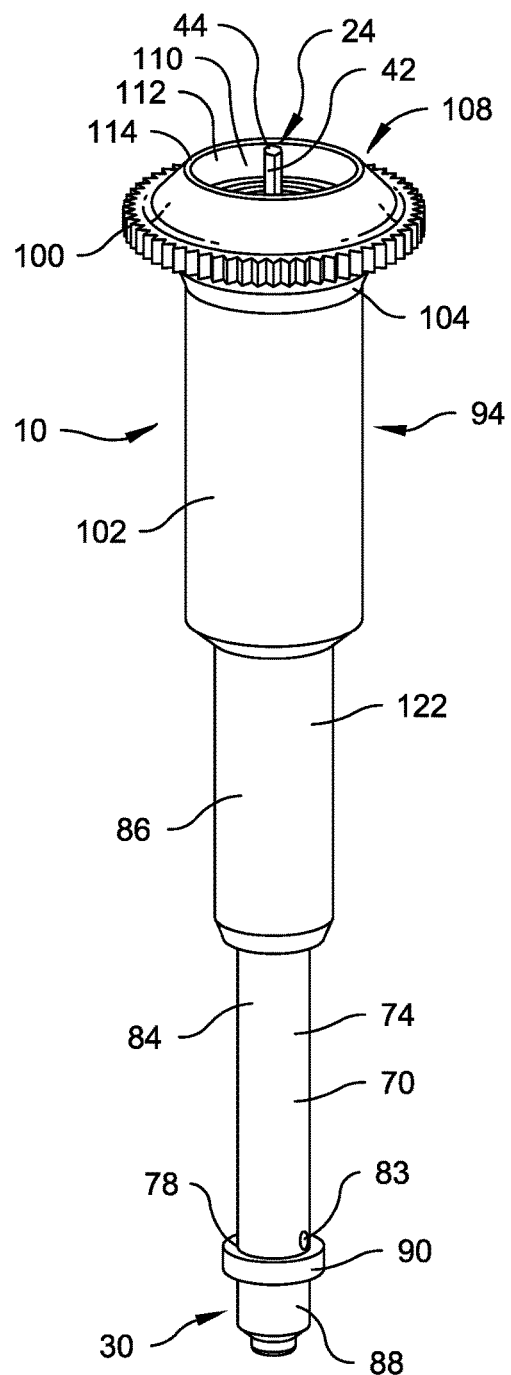
FIG. 3 is a front perspective view of the telescopic screw assembly of FIG. 1 in an expanded state.
Figure 4:
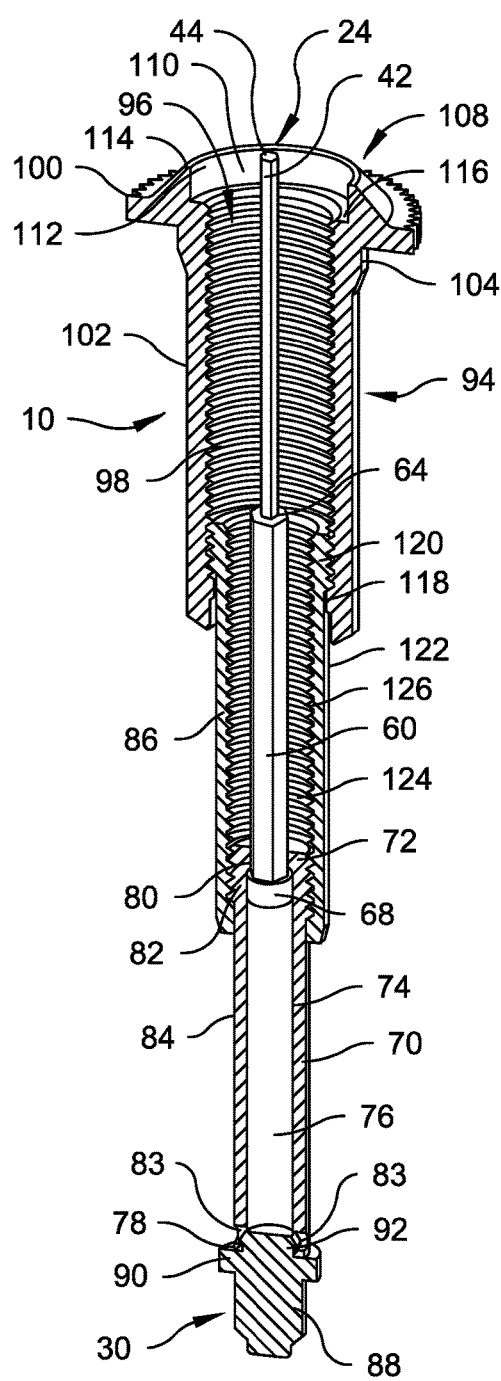
FIG. 4 is a perspective sectional view taken along line 2-2 of the telescopic screw assembly of FIG. 1 in an expanded configuration.

Certain terminology is used in the following description for convenience only and is not limiting. The words "right," "left," "lower," and "upper" designate directions in the drawings to which reference is made. The words "inwardly" or "distally" and "outwardly" or "proximally" refer to directions toward and away from, respectively, the geometric center or orientation of the telescopic screw assembly and related parts thereof. Unless specifically set forth herein, the terms "a", "an" and "the" are not limited to one element but instead should be read as meaning "at least one". The terminology includes the above-listed words, derivatives thereof and words of similar import.

It should also be understood that the terms "about," "approximately," "substantially" and like terms, used herein when referring to a dimension or characteristic of a component of the invention, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

The present invention relates to an injection assembly, and more particularly, to an injection assembly which includes a telescopic screw assembly, generally designated with reference numeral 10 in FIGS. 1-6. The telescopic screw assembly 10 is preferably positioned within an injection assembly housing 12 (FIG. 5) having a shell 14 with reinforcing ridges 16 extending generally perpendicularly away from the interior surface 18 of the shell 14. The housing 12 includes a cover (not shown) to cover the telescopic screw assembly 10 when the shell 14 and top are joined. The reinforcing ridges 16 give strength to the housing 12 to withstand compressive or other forces on the housing 12 and prevent damage to the telescopic screw assembly 10. Thus, the reinforcing ridges 16 are preferably manufactured of a material (e.g. high density polyethylene (HDPE), metal) strong enough to withstand any such forces. Some of the reinforcing ridges 16 are anchors 20 (see FIG. 6) which form a receiving area 22 for an anti-rotation shaft 24 of the telescopic screw assembly 10. The anchors 20 extend perpendicularly away from the interior surface 18 of the housing 12 and are generally parallel to each other. Alternatively, the anchors 20 can be other than parallel to each other to more closely follow the contour of the anti-rotation shaft 24. The distance between the anchors 20 can be adjusted during manufacture to accommodate the size of the anti-rotation shaft 24. The anchors 20 are preferably rigid to resist torque but may be somewhat deformable such that they conform to the shape of the anti-rotation shaft 24. Any of the ridges 16 can also be used to secure a motor (not shown) or other element associated with an injection assembly, as desired. Although only a single embodiment of a housing is discussed here, other housings are also contemplated for use. For example, another embodiment of a housing contemplated for use with the present invention is described in U.S. Pat. No. 8,465,455, the disclosure of which is incorporated by reference herein. The telescopic screw assembly 10 is secured within the housing 12 via the reinforcing ridges 16. Thus, the layout of the reinforcing ridges 16 can be adjusted to accommodate a telescopic screw assembly 10 of any shape or size.

Figure 5:
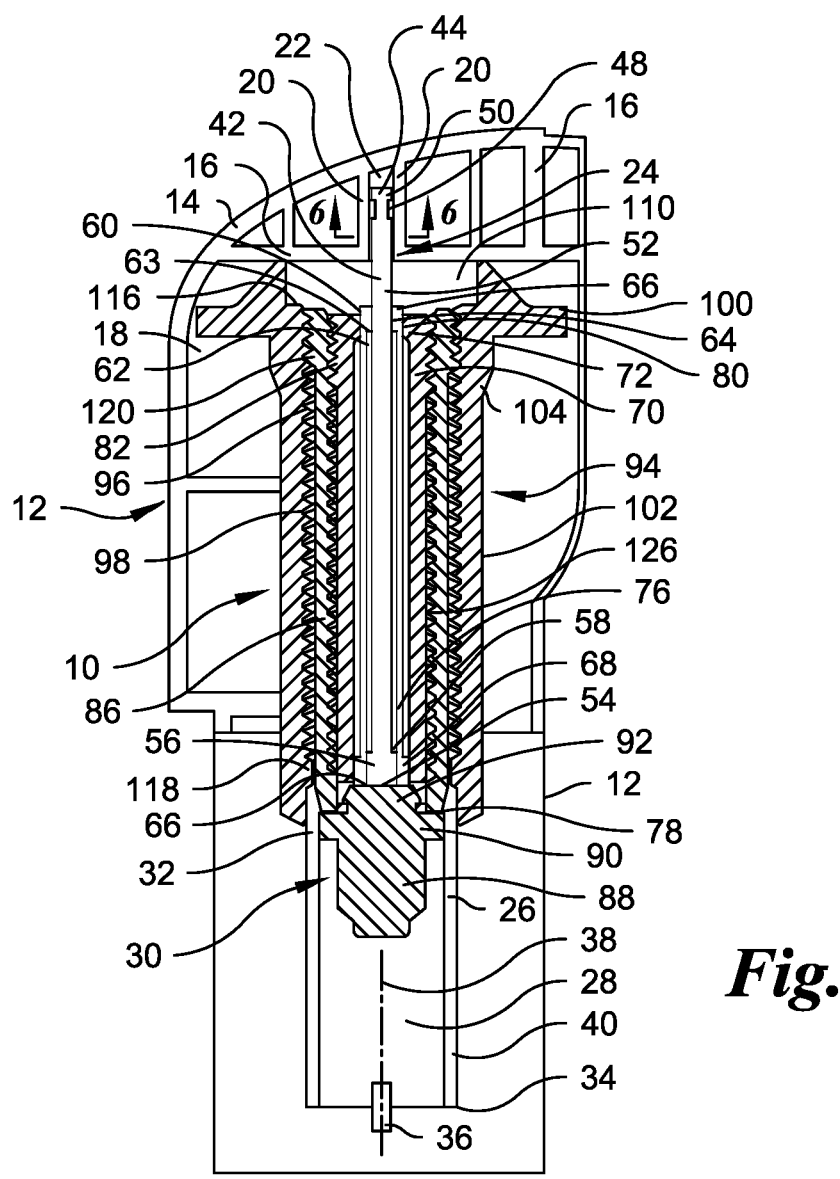
FIG. 5 is an enlarged front sectional elevational view of the telescopic screw assembly of FIG. 1 in an injection assembly.
Figure 6:
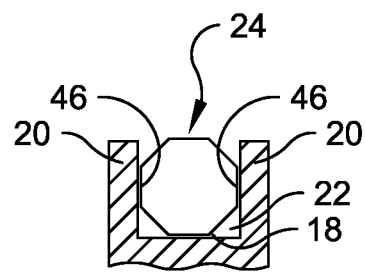
FIG. 6 is a sectional fragmentary view taken along line 6-6 of the telescopic screw assembly of FIG. 1 in the injection assembly of FIG. 5.

A barrel 26 is within the housing 12 in FIG. 5. The barrel 26 is a cylindrical member having an internal chamber 28 for storing medicine (not shown). Alternatively, the barrel 26 can have any desired cross-sectional shape (e.g. square, oval, any polygon). The size of the barrel 26 and the chamber 28 can be adapted as desired to accommodate dosages of various volumes. The cross-sectional shape of the chamber 28 is adapted to form a fluid tight seal with a plunger 30 such that the plunger 30 can force the medicine out of the chamber 28 as described below. A proximal end 32 of the barrel 26 is sealed by the plunger 30. A distal end 34 of the barrel 26 includes an outlet which in the present embodiment is a needle 36 such that as the plunger 30 advances along a proximal to distal axis 38 of the barrel 26, the medicine (not shown) is pushed out of the chamber 28 through the needle 36. Alternatively, the needle 36 can be connected to tubing (not shown) leading to a hypodermic needle (not shown) used to transfer the medicine (not shown) into the patient. In an alternative embodiment (not shown), the barrel 26 can be positioned such that the needle 36 extends from the housing 12 and directly injects the medicine (not shown) into the patient. The barrel 26 includes a wall 40 defining the chamber 28 and designed to withstand any pressure within the chamber 28 or medicine (not shown) when the plunger 30 is dispelling the medicine from the chamber 28. The barrel 26 is therefore preferably manufactured from acrylic, HDPE, metal, or similar material. Although the barrel 26 is shown as a separate element from the telescopic screw assembly 10, the two can be combined into a single canister (not shown) which is removably inserted into the housing 12 such that the combined single canister is a single use device.

The anti-rotation shaft 24 is preferably an elongate, telescoping shaft rotationally fixed to the housing 12 and preferably includes a first member 42 and a second member 60. A proximal end 44 of the first member 42 is positioned within the receiving area 22 of the housing 12 to prevent rotation of the anti-rotation shaft 24 (see FIG. 6). The first member 42 preferably has a non-circular (e.g. hexagon) cross-sectional shape but could also be square, rectangle, triangle, dodecagon, or any other multi-sided shape provided that the shape can prevent rotation of the first member 42 when the first member 42 is within the receiving area 22. The upright, parallel anchors 20 are each adjacent a face 46 of the first member 42 when the cross-sectional shape of the first member 42 has an even number of sides such that the flat surface of the anchors 20 are adjacent the flat surface of the face 46 thereby preventing rotation of the first member 42. The orientation of the anchors 20 can be adjusted as necessary such that at least two faces 46 of the first member 42 are confronted by the anchors 20 when the first member 42 has an odd number of sides. The proximal end 44 of the first member 42 further includes a neck 48 (best seen in FIG. 5) with a reduced cross-sectional diameter compared to adjacent regions of the first member 42. The receiving area 22 can include a flange (not shown) engaging the neck 48 to prevent rotation of the first member 42 while allowing limited movement of the first member 42 along the proximal to distal axis 38. Alternatively, the receiving area 22 may include a gasket (not shown but could be foam, rubber, etc. and may be flexible or rigid) surrounding the neck 48 to further prevent rotation of the first member 42 while also preventing axial movement of the first member 42. A head 50 is formed above the neck 48 and preferably has the same shape and dimensions as a body 52 of the first member 42. Alternatively, the head 50 and body 52 can have differing shapes or sizes, as desired. The distal end 54 of the first member 24 includes a foot 56 which extends radially from the body 52. The foot 56 is shown as having an annular perpendicular shelf 58 extending away from the body 52. Alternatively, the shelf 58 could extend away from the body 52 gradually (e.g. angled, curved, and the like) to reduce any stress concentrations at the transition between the body 52 and the foot 56. The foot 56 preferably includes a non-circular cross-sectional shape to prevent rotation of a second member 60 as explained below. Alternatively, the foot 56 may also have a circular cross section and not exhibit any of the anti-rotation features described herein, if desired. Although the foot 56 is shown on the distal end 66 of the second member 60, the foot 56 could be anywhere along the length of the second member 60. The length of the foot 56 as measured in the proximal to distal direction can be changed as desired but a foot 56 which extends closer to the proximal end 44 of the first member 42 limits the travel distance of the second member 60 as explained below.

The second member 60 has an elongate opening 62 adapted to receive the first member 42 and accommodate the foot 56. The elongate opening 62 preferably has a non-circular cross-sectional shape similar to the shape of the foot 56 of the first member 42. In FIGS. 1-6, the foot 56 and elongate opening 62 each have a dodecagon cross-sectional shape with the elongate opening 62 preferably sized at least slightly larger in diameter than the foot 56 such that the second member 60 can move relative to the first member 42 along a proximal to distal axis (not shown) but is prevented from rotating by the foot 56. Alternatively, the elongate opening 62 and foot 56 can have different cross-sectional shapes from each other provided that the shapes prevent relative rotation. In another alternative, the foot 56 and elongate opening 62 do not rotationally interfere with each other and the anti-rotation feature is provided by a proximal entryway 64 of the second member 60. The elongate opening 62 extends along a majority of the second member 60 in FIGS. 1-6 and through the distal end 66 of the second member 60. Alternatively, the elongate opening 62 may only be formed in a portion, or a minority, of the second member 60 and may terminate prior to reaching the distal end 66 of the second member 60. The proximal end 66 of the second member 60 includes a cap 63 (FIG. 5) extending inwardly and defining the proximal entryway 64. The proximal entryway 64 preferably is shaped similarly to, but is at least slightly larger than, the body 52 of the first member 42 such that the first member 42 is slidably axially positioned within the elongate opening 62 but is prevented from rotating by the body 52. The shapes of the proximal entryway 64 and body 52 can be any desired shape provided that their interaction prevents rotation (e.g. squares, triangles, dodecagons, square within a circle, octagon within a square, and the like). Alternatively, the proximal entryway 64 and body 52 could both have circular cross-sectional shapes that do not prevent rotation of the second member 60 with respect to the first member 42 and the anti-rotation feature is provided by the foot 56 within the elongate opening 62. The proximal entryway 64 preferably prohibits movement of the foot 56 past the proximal entryway 64. In other words, the second member 60 can move axially with respect to the first member 42 but the movement is limited when the shelf 58 of the foot 56 contacts the proximal entryway 64. This prevents disengagement between the first and second members 42, 60 as the telescopic screw assembly 10 expands.

The distal end 66 of the second member includes a stop 68 extending outwardly from the second member 60. The stop 68 has a circular cross-sectional shape but could also be dodecagonal, rectangular, oval, star-shaped, etc. The stop 68 is designed to fit within an inner screw 70 and prevent disengagement between the two. The second member 60 is axially translated when the stop 68 contacts a second portion 72 of the inner screw 70 and the inner screw 70 continues to move along the proximal to distal axis (not shown).

The inner screw 70 is preferably an elongate member having a body 74 defining an internal first portion 76 adapted to slidably receive the stop 68. Thus, the first portion 76 is preferably at least slightly larger than the stop 68 to allow the inner screw 70 to move with respect to the second member 60. The first portion 76 extends along a majority of the inner screw 70 in FIGS. 1-6. Alternatively, the first portion 76 may be less than a majority of the inner screw 70 and may terminate prior to the distal end 78 of the inner screw 70. The first portion 76 may be circular, oval, triangular, etc. in cross-section. The first portion 76 and stop 68 do not interact to provide anti-rotation features but could do so by adapting the shape of the stop 68 similarly to the shape of the foot 56 and elongate opening 62.

A second portion 72 is preferably formed at a proximal end 80 of the inner screw 70. The second portion 72 defines a passage which slidingly receives the second member 60. The passage of the inner screw 70 is preferably shaped similarly to, but slightly larger than, the second member 60 such that the interface between the second portion 72 and the second member 60 prevents relative rotation between the two. Thus, the first member 42 of the anti-rotation shaft 24 is rotationally fixed to the housing 12 and prevents the second member 60 and, in turn, the inner screw 70 from rotating during linear translation of one or more of the aforementioned members along the proximal to distal axis (not shown). The passageway of the second portion 72 can be any shape which prevents rotation and need not necessarily be the same shape as the second member 60. Alternatively, the second portion 72 and second member 60 need not prevent rotation and the anti-rotational feature can be provided by the stop 68 within the first portion 76.

An inner screw external thread (ISET) 82 is preferably formed on an outer surface 84 of the inner screw 70 at the proximal end 80. The ISET 82 extends along at least a portion of the inner screw body 74 but preferably does not extend all the way to the distal end 78 of the inner screw 70 such that the ISET 82 prevents the inner screw from exiting an intermediate screw 86 or outer screw 94, as explained below. At least one, and preferably two, apertures 83 are formed on the inner screw distal end 78 and are each adapted to receive a protrusion (not shown) from the plunger 30 to secure the plunger 30 to the distal end 78. The apertures 83 extend through the second member but could also extend only partially therethrough provided the apertures can receive the protrusions.

The plunger 30 is coupled to the inner screw distal end 78 and preferably includes a cylindrical base 88 with a collar 90 extending radially away from the base 88. The base 88 is sized to fit within the barrel 26 to force the medicine out of the chamber when the outer screw is rotated. The collar 90 is preferably cylindrical and has a diameter larger than the first portion 76 of the inner screw 70 to prevent the collar 90 from entering the first portion 76 by contacting the inner screw distal end 78. Alternatively, the base 88 could have a large enough diameter that the collar 90 is not necessary. The collar 90 is at least slightly larger in diameter than the inner diameter of the barrel 26 to provide a tight fit. A stem 92 extends upwardly from the collar 90 and into the inner screw first portion 76. The stem 92 includes at least one, and preferably two, protrusions (not shown) adapted to be inserted into the apertures 83. The protrusions secure the plunger 30 to the inner screw 70 and prevent relative rotation between the inner screw 70 and plunger 30. Alternatively, the plunger 30 may function as a cap which is coupled to a plunger of a closed system medicament canister (not shown).

Figures 7, 8:
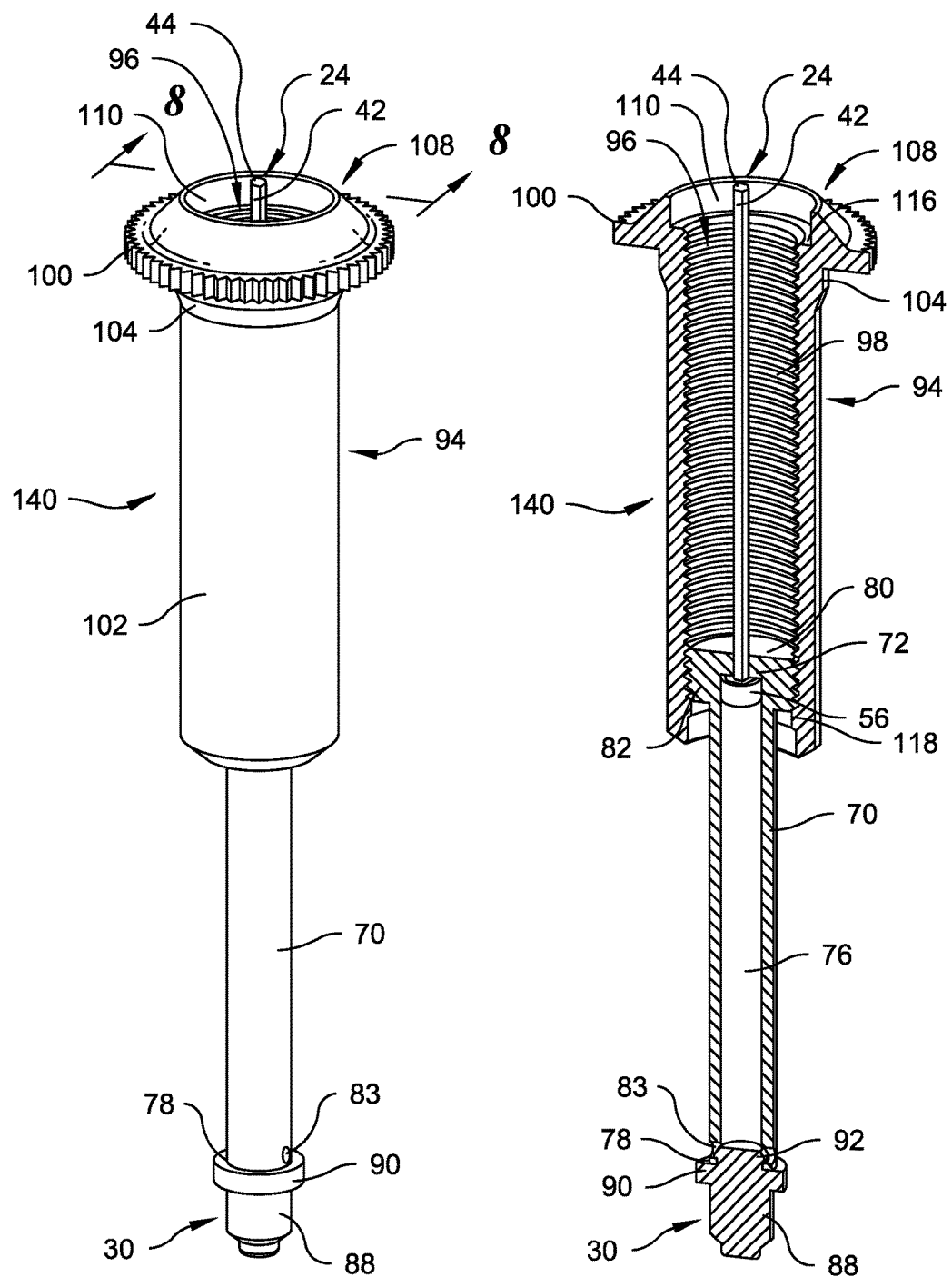
FIG. 7 is a perspective front view of a telescopic screw assembly in an expanded state in accordance with one embodiment of the present invention.
FIG. 8 is a front perspective sectional view along line 8-8 of the telescopic screw assembly of FIG. 7.

The telescopic screw assembly 10 includes an outer screw 94 which is rotatable with respect to the housing 12. The outer screw 94 has an outer screw opening 96 with an outer screw internal thread (OSIT) 98 to threadably receive the intermediary screw 86 (FIGS. 1-6). The intermediary screw 86 includes an intermediary screw outer thread (ISOT) 120 which preferably extends along a portion of the intermediary screw outer surface 122 and is adapted to engage the OSIT 98 such that rotation of the outer screw 94 relative to the intermediary screw 86 translates the intermediary screw 86 along the axis (not shown). The length of the ISOT 120 impacts the length of travel of the intermediary screw 86 as explained below. The inner screw 70 is moveable between a first position within the outer screw 94 (FIG. 2) and a second position at least partially extending from the outer screw 94 and may even be completely axially separated from the outer screw 94 (FIG. 4) when the outer screw is rotated (by a motor, manual user rotation, or the like). Alternatively, the intermediary screw 86 may be omitted and the outer screw opening 96 can receive the inner screw 70 such that rotation of the outer screw 94 directly translates the inner screw along the axis (not shown) and along the anti-rotation shaft 24 (FIGS. 7-8) via the engagement between the OSIT 98 and ISET 82. The OSIT 98 preferably extends along a majority of the outer screw opening 96 such that as the outer screw 94 is rotated, the intermediary screw 86 translates along the proximal to distal axis (not shown) as explained in greater detail below. The outer screw 94 rotates when a rotational force is applied to a gear 100 (e.g. spur gear, helical, and the like) on an outer surface 102 of the outer screw 94. The upper and lower edges of the gear 100 are preferably flat to such that the reinforcing ridges 16 of the housing can be positioned adjacent the lower edge of the gear 100 to prevent movement of the outer screw 94 during use of the telescopic screw assembly 10 (not shown). However, the upper and lower edges need not necessarily be flat in order to achieve this desired functionality and could be rounded, stepped, etc. as desired.

A neck 104 is formed between the outer screw body 106 and gear 100. The neck 104 includes a straight portion extending generally perpendicularly from the gear 100 and an angled portion connecting the straight portion to the outer surface 102 of the outer screw body 106. The reinforcing ridges 16 of the housing 12 can also be formed to receive the neck 104 to prevent movement of the telescopic screw assembly 10 during use (not shown).

A head 108 is formed above the gear 100. The head 108 has a frustoconical shape and defines an inner recess 110 which opens to the outer screw inner opening 96. The inner recess 110 is defined by an inner wall 112 extending downwardly from an upper rim 114. The upper rim 114 is preferably adjacent one of the reinforcing ridges (FIG. 5) when the telescopic screw assembly 10 is within the housing 12 to prevent movement of the outer screw 94 during use of the telescopic screw assembly 10. A shoulder 116 extends inwardly from the inner wall 112 to the outer screw opening 96. Although the shoulder 116 is shown as generally perpendicular to the inner wall 112 and outer screw opening axis (not shown), the shoulder 116 could be angled or rounded to facilitate easier loading of the intermediary screw 86 and inner screw 70 into the outer screw opening 96.

A detent 118 preferably extends annularly around the outer screw opening 96 at a lower end thereof and prevents the intermediary screw 86 from exiting the outer screw opening 96 as the intermediary screw 86 is threadably translated along the axis (not shown). The detent 118 may extend circumferentially around the entire outer screw opening 96 or, alternatively, may be only a single protrusion into the outer screw opening 96 provided that it prevents passage of the ISOT 120. The lower end of the outer screw 94 is preferably tapered to facilitate easier loading of the telescopic screw assembly 10 within the housing 12. Alternatively, the lower end could be other than tapered (e.g. rounded, flat, or the like).

The intermediary screw 86 is an elongate, cylindrical member positionable between the outer screw 94 and inner screw 70. The intermediary screw 86 is inserted into the outer screw opening 96 in FIGS. 1-6. Alternatively, the intermediary screw 86 could be any desired shape provided that it fits, and is able to rotate, within the outer screw opening 96. The ISOT 120 is formed at an upper end of the intermediary screw 86 on an outer surface 122 thereof and is threadably engageable with the OSIT 98. Alternatively, the ISOT 120 could be formed anywhere along the length of the intermediary screw 86, as desired. The intermediary screw 86 includes an intermediary screw opening 124 (best seen in FIG. 4) with a thread 126 formed thereon. The ISOT 120 and thread 126 have the same pitch but could have different pitches such that the telescopic screw assembly 10 expands in stages (e.g. the intermediary screw 86 is fully expanded before the inner screw 70 begins to expand or vice versa). The thread 126 is shown as extending along almost the entire length of the intermediary screw opening 124. However, the lower end of the intermediary screw opening 124 is unthreaded which prevents the inner screw 70 from exiting the intermediary screw opening 124 during use. The intermediary screw 86 is rotatable with respect to the housing 12 and is rotated by the outer screw 94 as the outer screw 94 is rotated by the motor (not shown).

In use, the telescopic screw assembly 10 is located within the housing 12 and medicine is within the chamber 28 of the barrel 26. The user activates the injection assembly such that the motor (not shown) rotates the gear 100, thus causing the outer screw 94 to rotate. As the outer screw 96 rotates with respect to the housing 12, one or both of the inner screw 70 and intermediary screw 86 begin to translate along the axis (not shown). The intermediary screw 86 translates when the outer screw 100 rotates with respect to the intermediary screw 86. The inner screw 70 translates when the intermediary screw 86 rotates with respect to the inner screw 70. The anti-rotation shaft 24 telescopically expands as the inner screw 70 and intermediary screw 86 translate along the axis (not shown). As the intermediary screw 86 rotates, it imparts a rotational force on the inner screw 70. However, the inner screw 70 is prevented from rotating by the anti-rotation shaft 24 which is rotationally fixed to the housing 12. The plunger 30 is also prevented from rotating by the anti-rotation shaft 24 because the plunger is fixed to the inner screw 70. The medicine is pushed out of the chamber 28 by the axially translating, rotationally fixed plunger 30 as the telescopic screw assembly 10 expands.

It will be appreciated by those skilled in the art that changes could be made to the embodiments described above without departing from the broad inventive concept thereof. It is understood, therefore, that this invention is not limited to the particular embodiment disclosed, but is intended to cover modifications within the spirit and scope of the present invention as defined by the appended claims.

We claim:
1. A injection assembly comprising:
a housing;
a barrel positioned in the housing, the barrel including a proximal end, a distal end, an axis extending between the proximal and distal ends, and a chamber for storing medicine;
an elongate anti-rotation shaft rotationally fixed to the housing, the shaft having a non circular cross section;
an inner screw having an inner screw opening configured to complementarily receive the anti-rotation shaft to prevent rotation of the inner screw with respect to the anti-rotation shaft but allow respective linear translation along the axis;
a outer screw rotatable with respect to the housing and having an outer screw opening to threadably receive the inner screw, wherein rotation of the outer screw translates the inner screw along the axis and along the anti-rotation shaft; and a plunger coupled to a distal end of the inner screw and moveable with respect to the chamber to push the medicine out of the chamber when the outer screw is rotated.

2. The injection assembly of claim 1, further comprising a gear fixed to an external surface of the outer screw such that rotation of the gear pushes the medicine out of the chamber.

3. The injection assembly of claim 1, wherein the inner screw is moveable between a first position within the outer screw and a second position at least partially extending from the outer screw.

4. The injection assembly of claim 1, further comprising a needle coupled to the chamber such that the plunger pushes the medicine through the needle as the plunger moves with respect to the chamber.

5. The injection assembly of claim 1, further comprising:
an inner screw external thread along at least a portion of an outer surface of the inner screw; and
an outer screw internal thread threadably coupled to the inner screw external thread.

6. The injection assembly of claim 5, further comprising:
an intermediary screw positionable between the outer screw and inner screw, the intermediary screw including an intermediary screw external thread engageable with the outer screw internal thread and an intermediary screw opening having an intermediary screw opening thread engagable with the inner screw external thread; wherein rotation of the outer screw axially translates and causes rotation of the intermediary screw; wherein rotation of the intermediary screw translates the inner screw along the axis.

7. The injection assembly of claim 1, wherein the anti-rotation shaft is a telescoping shaft and comprises:
a first member rotationally fixed to the housing; and
a second member having an elongate opening with the first member slidably positioned therein,
wherein the first member prevents rotation of the second member.

8. The injection assembly of claim 7, wherein the elongate opening is non-circular and receives a complementary non-circular shaped first member therein to prevent rotation of the second member with respect to the first member.

9. The injection assembly of claim 7, further comprising a stop coupled to the second member; and
wherein the inner screw opening includes a first portion adapted to slidably receive the stop, and a second portion adapted to slidably receive the second member while prohibiting passage of the stop through the second portion.

10. The injection assembly of claim 9, wherein the second member is adapted to be axially translated by the inner screw when the stop contacts the second portion.

11. A injection assembly comprising:
a housing;
a barrel positioned in the housing including a proximal end, a distal end, an axis extending between the proximal and distal ends, and a chamber for storing medicine;
an elongate anti-rotation shaft rotationally fixed to the housing, the anti-rotation shaft having a non-circular cross section;
an inner screw having an inner screw opening configured to complementarily receive the anti-rotation shaft to prevent rotation of the inner screw with respect to the anti-rotation shaft but allow respective linear translation along the axis, the inner screw including an inner screw external thread;
an intermediary screw including an intermediary screw external thread and an intermediary screw opening with an intermediary screw internal thread threadably engageable with the inner screw external thread such that rotation of the intermediary screw moves the inner screw along the axis and along the anti-rotation shaft;
an outer screw rotatable with respect to the housing and having an outer screw opening to receive the intermediary screw and including an outer screw internal thread engageable with the intermediary screw external thread such that rotation of the outer screw moves the intermediary screw along the axis and rotates the intermediary screw; and
a plunger coupled to a distal end of the inner screw and moveable with respect to the chamber to push the medicine out of the chamber when the outer screw is rotated.

12. The injection assembly of claim 11, further comprising a needle coupled to the chamber wherein the plunger pushes the medicine through the needle as the plunger moves with respect to the chamber.

13. The injection assembly of claim 11, wherein the inner screw is moveable between a first position at least partially within the outer screw and a second position axially spaced from the outer screw.

14. The injection assembly of claim 11, further comprising a gear fixed to an external surface of the outer screw such that rotation of the gear pushes the medicine out of the chamber.

15. The injection assembly of claim 11, wherein the inner screw is moveable between a first position within the outer screw and a second position at least partially extending from the outer screw.

16. The injection assembly of claim 11, wherein the anti-rotation shaft is a telescoping shaft and comprises: a first member rotationally fixed to the housing; and a second member having an elongate opening with the first member slidably positioned therein, the first member preventing rotation of the second member.

17. The injection assembly of claim 16, wherein the elongate opening is non circular and receives a complementary non-circular shaped first member therein to prevent rotation of the second member with respect to the first member.

* * * * *